(12) United States Patent
Anderson et al.

(10) Patent No.: US 8,877,872 B2
(45) Date of Patent: Nov. 4, 2014

(54) SWITCHABLE IONIC ADHESIVE COATING FOR RECYCLABLE CARBON FIBER

(75) Inventors: Kraig Anderson, Burlingame, CA (US); Angele Sjong, Louisville, CO (US)

(73) Assignee: Empire Technology Development LLC, Wilmington, DE (US)

( * ) Notice: Subject to any disclaimer, the term of this patent is extended or adjusted under 35 U.S.C. 154(b) by 0 days.

(21) Appl. No.: 13/882,424

(22) PCT Filed: Aug. 30, 2012

(86) PCT No.: PCT/US2012/053040
§ 371 (c)(1),
(2), (4) Date: Apr. 29, 2013

(87) PCT Pub. No.: WO2014/035393
PCT Pub. Date: Mar. 6, 2014

(65) Prior Publication Data
US 2014/0066576 A1    Mar. 6, 2014

(51) Int. Cl.
*C08G 63/00* (2006.01)
*C08F 8/32* (2006.01)
*C07C 277/08* (2006.01)

(52) U.S. Cl.
CPC .................................. *C07C 277/08* (2013.01)
USPC ........ 525/374; 564/236; 525/326.1; 525/376; 525/437

(58) Field of Classification Search
CPC ........ C08G 63/64; C08G 63/52; C08G 63/02; C08G 63/06; C08G 63/12; C08G 63/16; C08G 63/40; C08G 18/56; C08G 71/04
USPC ................ 525/326.1, 376; 564/236
See application file for complete search history.

(56) References Cited

U.S. PATENT DOCUMENTS

| | | | |
|---|---|---|---|
| 5,069,971 A | | 12/1991 | Waketa et al. |
| 5,106,680 A | * | 4/1992 | King et al. .................. 428/300.1 |
| 5,128,425 A | | 7/1992 | Shiraishi et al. |
| 5,900,311 A | * | 5/1999 | Campanella et al. ......... 428/215 |
| 2006/0134413 A1 | | 6/2006 | Wilkinson |
| 2006/0217482 A1 | * | 9/2006 | Lukehart et al. ............... 524/495 |
| 2007/0276082 A1 | * | 11/2007 | Balfour et al. ................. 524/505 |
| 2008/0058549 A1 | | 3/2008 | Jessop et al. |
| 2011/0130524 A1 | | 6/2011 | Wittenbecher et al. |

OTHER PUBLICATIONS

Oswald (International Plastic Handbook, p. 605-607, 2006).*
Amemiya et al., "Aminosilane multilayer formed on a single-crystalline diamond surface with controlled nanoscopic hardness and bioactivity by a wet process," 2009, Langmuir 25(1), pp. 203-209.
Bonduelle and Gillies, "Dendritic Guanidines as Efficient Analogues of Cell Penetrating Peptides," 2010, Pharmaceuticals 3, pp. 636-666.
Ehlert et al., "Carboxyl functionalization of carbon fibers through a grafting reaction that preserves fiber tensile strength," Carbon 49, 2011, pp. 4246-4255.
Grotz et al. "Sensing external spins with nitrogen-vacancy diamond" 2011, New J. Phys. 13, 055004, 8 pages.
Hernando et al., "Immobilization of horseradish peroxidase via an amino silane on oxidized ultrananocrystalline diamond," 2007, Diamond and Related Materials 16, pp. 138-143.
International Search Report and Written Opinion received for PCT/US12/53040 mailed Jan. 18, 2013.
Jessop et al., "A solvent having switch able hydrophilicity," 2010, Green Chem. 12, pp. 809-814.
Li, et al., "Functionalization of carbon nanofibers with diamine and polyimide oligomer," Jan. 24, 2008, Carbon 46(8), pp. 1115-1125.
Liu, Zhi-feng, et al., "Recycling Waste Printed Circuit Board with Supercritical CO2 Fluid," 2008, Environmental Science & Technology, 31 (1), pp. 83-86.
Mihich et al., "Inhibitory Effect of Decamethylene Diguanidine against Leukemia L1210 and Sarcoma 180," 1960, Cancer Res 20, pp. 609-612.
Morgan, "Carbon Fibers and Their Composites," CRC Press, Boca Raton, FL, 2005, pp. 403-405.
Plaseied et al., "Effects of Carbon Nanofiber Content and Surface Treatment on the Mechanical Properties of Vinyl Ester," 2008, Polymers and Polymer Composites, 16(7), pp. 405-413.
Zhao et al. "Formation of a carbon fiber/polyhedral oligomeric silsesquioxanejcarbon nanotube hybrid reinforcement and its effect on the interfacial properties of carbon fiber/epoxy composites," 2011, Carbon 49, pp. 2624-2632.
Kumagai, et al., "An Efficient Synthesis of Bicyclic Amidines by Intramolecular Cyclization," Angew. Chem. Int. Ed., vol. 43, No. 4, pp. 478-482, (2004).

* cited by examiner

*Primary Examiner* — Randy Gulakowski
*Assistant Examiner* — Christopher M Rodd
(74) *Attorney, Agent, or Firm* — Foley & Lardner LLP

(57) ABSTRACT

The present technology provides an carbon fiber reinforced plastic having an organoamine coated carbon fiber and a carbonyl functionalized matrix polymer. Also described is a method for recycling the carbon fiber reinforced plastic using an acidic gas.

19 Claims, No Drawings

SWITCHABLE IONIC ADHESIVE COATING FOR RECYCLABLE CARBON FIBER

CROSS-REFERENCE TO RELATED APPLICATIONS

This application claims the benefit of International Application Serial No. PCT/US2012/053040, filed on Aug. 30, 2012, which is incorporated herein by reference in its entirety for any and all purposes.

FIELD

The present technology relates generally to a composition of a carbon fiber reinforced plastic (CFRP) and to a method for recycling of carbon fibers from a CFRP. Specifically, the present technology provides recycling methods that are relatively inexpensive and permit the release of a carbon fiber from the CFRP without damage and in high yield.

BACKGROUND OF THE INVENTION

Carbon fiber (CF) is a material that includes fibers composed mostly of carbon atoms and having a diameter from about 5 μm to about 10 μm. The properties of carbon fibers, such as high stiffness, high tensile strength, low weight, high chemical resistance, high temperature tolerance and low thermal expansion, make them very popular, for example, in civil, aerospace and mechanical engineering applications, in the manufacture automobiles, and the manufacture of high performance sport gear.

Carbon fibers are usually combined with other materials to form a composite. When combined with a plastic resin and wound or molded it forms carbon fiber reinforced plastic (CFRP), an extremely rigid material having a very high strength-to-weight ratio. However, carbon fibers are relatively expensive when compared to glass fibers or plastic fibers. Thus, it is desirable to recycle the carbon fiber from unwanted CFRP prior to disposal. However, current methods for recycling carbon fibers from CFRP are tedious, expensive and most importantly damage the structural integrity of the recycled fiber, often making the recycled carbon fiber unsuitable for reuse.

SUMMARY OF THE INVENTION

The present technology relates to compositions of carbon fiber reinforced plastics and to methods for recycling carbon fiber from such plastics by releasing the carbon fiber from the surrounding plastic resin without damaging the fiber. According to an embodiment, the carbon fiber reinforced plastic matrix includes at least one surface functionalized carbon fiber; and at least one carboxylic acid functionalized matrix polymer. The carbon fiber of the CFRP matrix is surface functionalized, moreover, with one or more organoamine groups.

According to one embodiment, the organoamine is attached to the carbon fiber using a ($C_1$-$C_{10}$)alkylene linker or a polyethylene glycol linker. Examples of linkers include without limitation —($C_1$-$C_{10}$)alkylene-NH—, ($C_1$-$C_{10}$)alkylenesiloxy, —($C_1$-$C_{10}$)alkylene-C(O)—, or a —(OCH$_2$—CH$_2$)—O— group. Subscript "n" in the formula illustrated above is an integer from 0 to 10.

For carbon fiber reinforced plastics according to the present technology, examples of organoamines include without limitation an amidine, a polyamine, a polyguanidine, a diguanidine, a guanidine, ($C_1$-$C_6$)alkylene diamine, or a —NH$_2$-functionalized dendrimer group. In some embodiments, the organoamine includes compounds selected from 1,3-diaminopropane, 1,1'-((ethylimino)bis(trimethylene)) diguanidine, guanidine dendrimer, 3-aminopropylsiloxy, 1,6-diaminohexane, or a diethylamine group.

As described above the surface of the matrix polymer is functionalized to have carboxylic acid groups. According to one aspect of the present technology the matrix polymer is a thermoplastic polymer selected from the group consisting of polyacetals, nylons, polyethylene terpthalate (PET) and copolymers thereof.

The present technology also provides a method for making a carbon fiber reinforced plastic matrix. In accordance with an aspect of this technology, therefore, the method includes contacting at least one surface functionalized carbon fiber with at least one carboxylic acid functionalized matrix polymer to obtain the carbon fiber reinforced plastic matrix, where the surface of the carbon fiber is functionalized with one or more organoamines.

According to one embodiment of the present technology, at least one surface of the carbon fiber is oxidized to obtain a carboxylic acid functionalized carbon fiber before contacting with one or more organoamines or organoamine precursors to provide the carbon fiber surface functionalized with one or more organoamines. In some embodiments, the technology provides the use of a linker, such as a ($C_1$-$C_{10}$)alkylene linker to conjugate the organoamine to the carboxylic acid functionalized carbon fiber.

In yet another embodiment, at least one surface of the carbon fiber is oxidized to obtain a functionalized carbon fiber having a mixture of carboxylic acid and ester groups. These surface carboxylic acid and ester groups can reduced to hydroxyl groups before contacting with an organoamine or an organoamine precursor. Alternatively, the surface ester groups are hydrolyzed to carboxylic acid groups prior to their contact with an organoamine or organoamine precursor.

For example, hydroxyl groups on the surface of the carbon fiber can be contacted with an amino($C_1$-$C_{10}$)trialkoxysilane moiety to provide an organoamine functionalized carbon fiber. Examples of amino($C_1$-$C_{10}$)trialkoxysilanes include without limitation 3-aminopropyltrimethoxysilane, ((6-aminohexyl)aminomethyl)triethoxysilane, or diethylaminomethyltriethoxysilane groups.

According to yet another embodiment the hydroxyl groups on the surface of the carbon fiber are contacted with a halo ($C_1$-$C_{10}$)alkylenetrialkoxysilane, for example, a 3-bromopropyl trimethoxysilane or 3-iodopropyltrimethoxysilane to provide a halo($C_1$-$C_{10}$)alkylenesiloxy functionalized carbon fiber which is further contacted with one of the aforementioned organoamines.

Also provided by the present technology is a method for recycling a carbon fiber reinforced plastic matrix. In an embodiment of this technology, the method includes contacting the carbon fiber reinforced plastic matrix with an acid to decompose the matrix. The carbon fiber is separated from the decomposed matrix to obtain recycled carbon fiber. The carbon fiber reinforced plastic matrix used by the present technology includes at least one surface functionalized carbon fiber whose surface is functionalized with one or more organoamines and at least one carboxylic acid functionalized matrix polymer.

According to an aspect of this technology, the carbon fiber reinforced plastic matrix is contacted with the acid in the presence of a polar protic solvent. Examples of polar protic solvents include water, a linear or branched ($C_1$-$C_{10}$) alcohols, carboxylic acids, or mixtures thereof. The acid used to promote decomposition of the carbon fiber reinforced plastic matrix can be in gaseous form and is selected from sulfur dioxide, supercritical carbon dioxide, carbonyl sulfide, carbon disulfide, boron trifluoride, nitrogen dioxide, phosphorous pentafluoride, hydrogen chloride, hydrogen fluoride, or hydrogen bromide. After separation of the carbon fiber from the decomposed matrix, the surface of the recycled carbon fiber is re-functionalized prior to use.

The foregoing summary is illustrative only and is not intended to be in any way limiting. In addition to the illustrative aspects, embodiments, and features described above, further aspects, embodiments, and features will become apparent by reference to the following detailed description.

DETAILED DESCRIPTION OF THE PREFERRED EMBODIMENTS

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

The ability to recycle carbon fibers by decomposing a carbon fiber reinforced plastic matrix depends in large part on the chemical nature of interactions between the surface of the matrix or resin and the surface of the carbon fiber. Often, it becomes necessary to functionally modify the surface of the carbon fiber to promote adhesion between the carbon fiber and a matrix resin, such as an epoxy material used to form a carbon fiber reinforced plastic.

Such functional modification of the carbon fiber's surface includes the introduction of oxygen containing species, such as carbonyl groups (—C(O)—), carboxylic acid (—COOH), carboxylic acid anhydrides, hydroxyl (—OH), or ester (—COOR) groups onto the surface of the carbon fiber. Both chemical and electrochemical means are used to functionalize the carbon fiber surface. Chemical treatment includes without limitation the use of strong inorganic and organic acids, such as sulfuric acid, nitric acid and perchloric acid, while electrochemical oxidation utilizes an aqueous electrochemical bath and oxygen as a cheap and convenient way to functionalize the fiber's surface.

The present technology provides a carbon fiber reinforced plastic that is readily recycled to provide undamaged carbon fibers that can be reused. Recycling and recovery of carbon fibers from a carbon fiber reinforced plastic matrix according to the present technology is facilitated by the ability to selectively modulate interactions that hold the organoamine functionalized carbon fiber to a carboxylic acid functionalized matrix.

In one embodiment, therefore, the present technology provides a covalently attached carbon fiber coating. The carbon fiber coating according to the present technology has several advantages. The coating functions as a sizing layer, enhances fiber lubrication and provides an anti-static property that abets fiber handling. The carbon fiber coating according to the present technology also improves non-covalent adhesion of the fiber to the surface of the matrix during the manufacture of the carbon fiber reinforced plastic. Moreover, carbon fibers whose surfaces are coated using the coating of the present technology can readily be recycled without damaging the recycled carbon fiber.

According to one embodiment, therefore, the present technology provides an organoamine based carbon fiber coating that can be covalently attached to the carbon fiber. In the context of the present technology, the term "organoamine" refers to any functional group containing at least one basic nitrogen atom which is attached to at least one carbon atom. In some embodiments the organoamines include —$NH_2$, ($C_1$-$C_{10}$)alkyl amines, ($C_1$-$C_{10}$)alkyl diamines, ($C_3$-$C_{14}$)aromatic amines, polyamines, nitrogen-containing heterocycles as well as nitrogen-containing heteroaromatic compounds.

Alkyl groups include straight chain and branched alkyl groups having from 1 to 10 carbon atoms or, in some embodiments, from 1 to 9, 1 to 8, 1 to 6, or 1 to 4 carbon atoms. Alkyl groups further include cycloalkyl groups. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. The terms "substituted aminoalkyl" or "substituted alkyl amine" include straight chain and branched alkyl groups having from 1 to 10 carbon atoms in which at least one hydrogen atom is replaced by an amino (—$NH_2$) group. Examples of ($C_1$-$C_{10}$)alkyl amines include without limitation, methylamine, ethylamine propylamine, iso-propoylamine, butylamine, sec-butylamine, iso-butylamine and hexylamine.

Alkyl diamines are straight chain and branched alkyl groups having from 1 to 10 carbon atoms in which two hydrogen atoms are replaced by an amino (—$NH_2$) group. Alkyl diamines include compounds in which a hydrogen atom from each of the terminal methyl (—$CH_3$) groups is replaced by an amino (—$NH_2$) group. Alternatively, alkyl diamines include compounds in which a hydrogen from one of the terminal methyl group and a hydrogen atom of one of the methylene groups within the alkyl chain are replaced by an amino (—$NH_2$) group. Within the class ($C_1$-$C_{10}$)alkyl diamines are included without limitation 1,3-proylamine, 1,4-butylamine, 1,3-butylamine, 1,6 hexylamine and the like.

Aryl groups, also known as aromatic groups, are cyclic aromatic hydrocarbons of 6 to 14 carbons that do not contain heteroatoms. Aromatic groups herein include monocyclic, bicyclic and tricyclic ring systems. Thus, aromatic groups include, but are not limited to, phenyl, azulenyl, heptalenyl, biphenyl, fluorenyl, phenanthrenyl, anthracenyl, indenyl, indanyl, pentalenyl, and naphthyl groups. In some embodiments, aromatic groups contain from 6 to 12 or even 6 to 10 carbon atoms in the ring portions of the groups. In some embodiments, the aromatic groups are phenyl or naphthyl. The phrase "aromatic groups" includes groups containing fused rings, such as fused aromatic-aliphatic ring systems (e.g., indanyl, tetrahydronaphthyl, and the like). Within the class of aromatic amines are included without limitation aniline, 1,4-diaminobenzene, o-tohuidine, 2,4,6-trimethylamine, anisidine and N-methylaniline.

The term "heterocyclyl" or "heterocycle" as used herein refers to non-aromatic ring compounds containing 3 to 14 ring members, of which one or more is a heteroatom such as, but not limited to, N, O, P and S. In some embodiments, heterocyclyl groups include 3 to 6, 3 to 10, 3 to 12, or 5 to 6 ring members. Heterocyclyl groups encompass partially unsaturated and saturated ring systems, such as, for example, imidazolinyl and imidazolidinyl groups. The phrase "heterocyclyl group" includes fused rings and may include an aromatic group fused to a non-aromatic group, e.g. dihydrobenzofuran. The phrase also includes bridged polycyclic ring systems containing a heteroatom such as, but not limited to, quinuclidinyl. However, the phrase does not include heterocyclyl groups that have other groups, such as alkyl, oxo or halo groups, bonded to one of the ring members. Rather, these are referred to as "substituted heterocyclyl groups". Heterocyclyl groups include, but are not limited to, aziridinyl, azetidinyl, pyrrolidinyl, imidazolidinyl, pyrazolidinyl, thiazolidinyl, tetrahydrothiophenyl, tetrahydrofuranyl, dioxolyl, piperidinyl, piperazinyl, morpholinyl, thiomorpholinyl, tetrahydropyranyl, tetrahydrothiopyranyl, quinuclidinyl groups. Representative substituted heterocyclyl groups may be mono-substituted or substituted more than once, such as, but not limited to, piperidinyl or morpholinyl groups, which are 2-, 3-, 4-, 5-, or 6-substituted, or disubstituted with various substituents such as those listed above. Nitrogen-containing heterocycles are heterocyclyl groups that include at least one ring member which is a nitrogen atom. Nitrogen-containing heterocycles include without limitation aziridines, azetidines, pyrrolidine, imidazolidine, pyrazolidine and piperidine.

The term "heteroaryl" or "heteroaromatic" group as used herein refers to aromatic ring compounds containing 5 to 14 ring members, of which, one or more is a heteroatom such as, but not limited to, N, O, P and S. Heteroaryl groups can have one, two or three rings. Heteroaryl groups therefore include, but are not limited to, groups such as pyrrolyl, pyrazolyl, triazolyl, tetrazolyl, oxazolyl, isoxazolyl, thiazolyl, pyridyl, pyridazinyl, pyrimidinyl, pyrazinyl thiophenyl benzothiophenyl, furanyl, benzofuranyl, indolyl, azaindolyl (pyrrolopyridyl), indazolyl, benzimidazolyl, imidazopyridyl (azabenzimidazolyl), pyrazolopyridyl, triazolopyridyl, benzotriazolyl, beuzoxazolyl, benzothiazolyl, benzothiadiazolyl, imidazopyridyl, isoxazolopyridyl, thianaphthalenyl, purinyl, xanthinyl, adeninyl, guaninyl, quinolinyl, isoquinolinyl, tetrahydroquinolinyl, quinoxalinyl, and quinazolinyl groups. Although the phrase "heteroaryl groups" includes fused ring compounds such as indolyl and 2,3-dihydro indolyl, the phrase does not include heteroaryl groups that have other groups bonded to one of the ring members, such as alkyl groups. Rather, heteroaryl groups with such substitution are referred to as "substituted heteroaryl groups." Representative substituted heteroaryl groups may be substituted one or more times with various substituents such as those listed above. Nitrogen-containing heteroaromatics include heteroaryl groups with at least one ring member which is nitrogen. Nitrogen-containing heteroaromatics include, without limitation pyridine, pyrrole, imidazole, pyrazole, pyrazine, pyrimidine, pyridazine, 1,2,3-triazine, 1,2,4-triazine 1,3,5-triazine and tetrazole.

Within the context of the present technology, the term "polyamine" refers to a compound having two or more amino groups that are separated from each other by at least one methylene group. For example, compounds encompassed by the following formula —$NH_2$—[$(CH_2)_x$—$NH$]$_y$—$CH_2$—$NH_2$, where subscripts "x" and "y" are each independently non-negative integers from 0 to 10, fall within the polyamine class. Examples of polyamines include without limitation diethylamine, dipropylamine, putrescine, spermidine and spermine.

According to an embodiment of the technology, the organoamine can be an amine containing dendrimer or a dendrimer having multiple guanidine groups on its surface. The use of a dendrimer as the organoamine may have certain advantages since it is possible to fine tune the chemical properties of a dendrimer by altering the dendrimer backbone, the number of guanidine or amine surface groups, the connectivity between dendrons and by altering the generation number of a dendrimer. Examples of amine containing dendrimers include polyamidoamine (PAMAM) dendrimer and the polypropylene imine (PPI) dendrimers. Both dendrimers are available commercially in different generation numbers and their surface amine groups can be further modified to guanidine groups using protocols described in the literature. See Bonduelle et al., *Pharmaceuticals*, Vol. 3, (2010), pp 636-666.

A "guanidine" within the context of this technology refers to a molecule that is chemically represented by the following structure: $R_1N$=$C(NR_2R_3)(NR_4R_5)$, where $R_2$, $R_3$, $R_4$ and $R_5$ are independently hydrogen, ($C_1$-$C_{10}$)alkyl($C_3$-$C_{14}$)cycloalkyl, siloxy, or ($C_6$-$C_{14}$)aryl groups. For certain embodiments, when $R_2$, $R_3$, $R_4$ and $R_5$ are independently ($C_1$-$C_{10}$) alkyl, ($C_3$-$C_{14}$)cycloalkyl, or ($C_6$-$C_{14}$)aryl groups, these groups are optionally substituted with one or more siloxyl groups according to the formula —$Si(R_6)$, —O— and $R_6$ in such embodiments is a substituted or unsubstituted alkyl, cycloakyl, aryl, or alkoxy group. Some examples of guanidines include without limitation N,N,N'N'-tetramethylguanidine, N,N,N'N'tetramethyl-N",N"-phenylguanidine and 2-butyl-1,1,3,3-tetramethylguanidine. In other embodiments, $R_2$, $R_3$, $R_4$ and $R_5$ can independently be a siloxy group that is substituted with one or more groups selected from ($C_1$-$C_{10}$)alkyl, ($C_3$-$C_{14}$)cycloalkyl, or ($C_6$-$C_{14}$)aryl. Alternatively. $R_2$ and $R_3$ taken together with the nitrogen to which they are bonded, can form a nitrogenous heteroaryl or cycloaliphatic ring. Likewise, $R_4$ and $R_5$ taken together with the nitrogen to which they are bonded, can form a nitrogenous heteroaryl or cycloaliphatic ring.

The term "siloxy" refers to a compound of formula —$Si(R_6)(R_7)$—O—. $R_6$ and $R_7$ are independently selected from —H, or a substituted or unsubstituted alkyl, cycloalkyl, alkoxy, or aryl. In some embodiments, $R_6$ and $R_7$ are independently cycloalkyl, such as a ($C_3$-$C_{14}$)cycloalkyl group. Thus, a "siloxyl" group or chain can include {$Si(aliphatic)_2$-O} units, {$Si(aryl)_2$-O} units, or {$Si(aliphatic)(aryl)$-O}units. In the present context, "aliphatic" refers to acyclic or cyclic non-aromatic compounds, for example, optionally substituted ($C_1$-$C_{10}$)alkyl, ($C_3$-$C_{14}$)cycloalkyl. According to one embodiment, the siloxyl group is an alkyl-siloxyl group having $C_n(SiO)_m$ units, where n is a number from 0 to 4, m is a number from 0 to 2, and n+m≤4, for example, a group having {$Si(CH_3)_2$—O}units. Exemplary of an aryl-siloxyl or alkyl-arylsiloxyl group, moreover, are ($Si(C_6H_5)_2$—O) or {$Si(CH_3$—$C_6H_5)_2$—O}, respectively.

The term "cycloalkyl" refers to cyclic alkyl groups such as, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Cycloalkyl groups further include mono-, bicyclic and polycyclic ring systems, including for example bridged cycloalkyl groups and fused rings.

Alkoxy groups are hydroxyl groups (—OH) in which the bond to the hydrogen atom is replaced by a bond to a carbon atom of an alkyl group. Examples of linear alkoxy groups include but are not limited to methoxy, ethoxy, propoxy, butoxy, pentoxy, hexoxy, and the like. Examples of branched alkoxy groups include but are not limited to isopropoxy, sec-butoxy, tert-butoxy, isopentoxy, isohexoxy, and the like.

An "amidine" refers to a molecule that is chemically represented as follows: $R_1N$=$CR_2(NR_3R_4)$, where $R_1$, $R_2$, $R_3$ and $R_4$ are hydrogen, ($C_1$-$C_{10}$)alkyl, ($C_3$-$C_{14}$)cycloalkyl, siloxy, ($C_6$-$C_{14}$)aryl and aliphatic-siloxyl groups. According to one embodiment, when $R_1$, $R_2$, $R_3$ and $R_4$ are independently ($C_1$-$C_{10}$)alkyl, ($C_3$-$C_{14}$)cycloalkyl, or ($C_6$-$C_{14}$)aryl groups, these groups are optionally substituted with one or more siloxyl groups according to the formula —$Si(R_6)_2$—

O—, and $R_6$ in such embodiments is a substituted or unsubstituted alkyl, cycloakyl, aryl, or alkoxy group. Alternatively, $R_3$ and $R_4$ together with the nitrogen to which they are bonded, can form a nitrogenous heteroaryl or cycloaliphatic ring.

Examples of amidines include without limitation 1,8-diazabicycloundec-7-ene (DBU), 1,5-diazabicyclo[4.3.0]non-5-ene, 2,3,4,6,7,8,9,10-octahydropyrimidol[1,2-a]azepine, pyridine-3-amidine, as well as the amidines illustrated below.

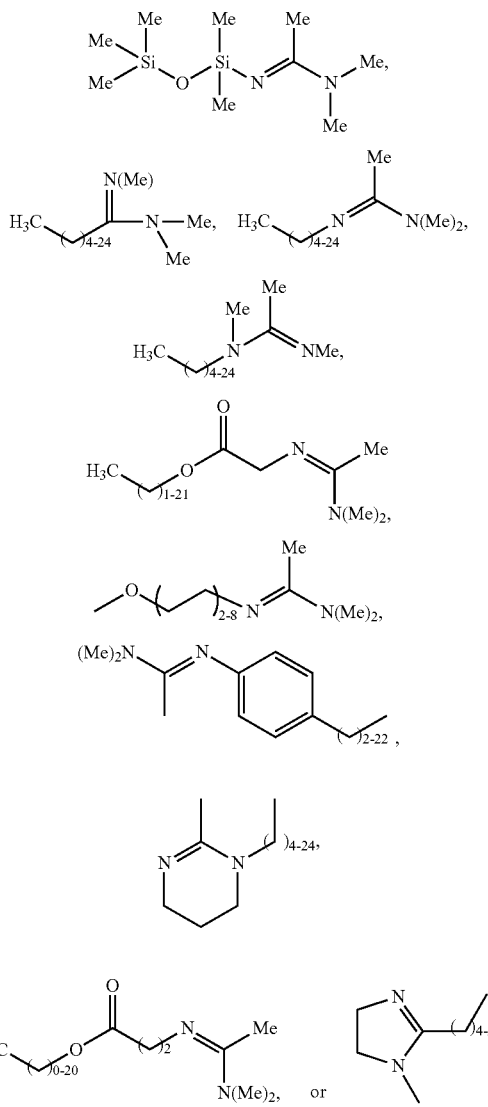

Various methodologies can be used to couple amidines to the CF surface. For example, cyclic amidines such as DBU can be covalently coupled to the CF surface using the azide-alkyne "click" chemistry. Alternatively, Suzuki coupling or Stille coupling chemistries can be employed for conjugating an amidine to the CF surface.

In one embodiment, an alkyl-alkyl Suzuki cross-coupling reaction will be employed to couple a halo-substituted cyclic amidine and a 9-BBN functionalized CF surface as illustrated in Scheme 1 below and described in the literature. See Saito et al. *J. Am. Chem. Soc.* 2007 129 9602-9603.

Scheme 1

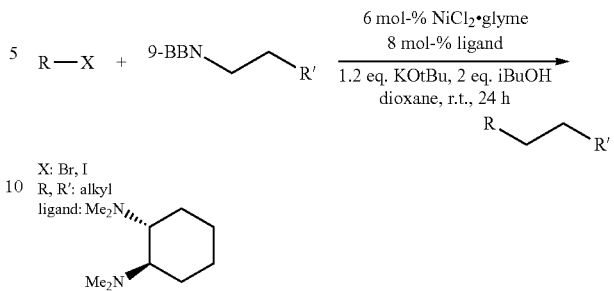

The halo substituted cyclic amidine can be synthesized from a hydroxyl-substituted amidine using the method of Kumagai et al. See Kumagai et al. *Angew. Chem. Int. Ed.* 2004 43 478-482 and Scheme 2.

Scheme 2

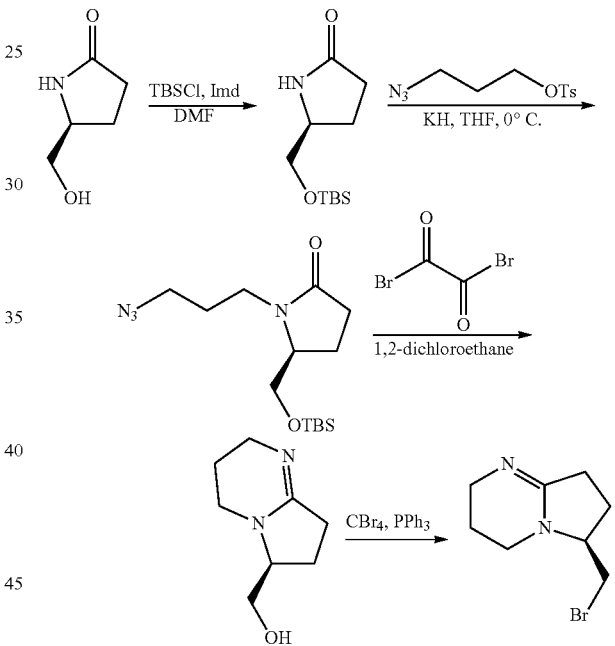

Briefly, the commercially available hydroxyl-substituted lactam (5-(hydroxymethyl)pyrrolidin-2-one, will be protected using an alkylsilyl halide such as t-butyldimethyl silyl chloride, in the presence of a base such as imidazole, and using a polar aprotic solvent such as dimethyl formamide. The amino group of the resulting TBS protected lactam will then be reacted with a tosylated alkyl azide such as 1-tosyl-3-azopropane in the presence of an alkali hydride (e.g., potassium hydride (KH)) in tetrahydrofuran at reduced temperature. Reaction with oxalyl dibromide followed by cyclization and subsequent deprotection will give the corresponding hydroxymethyl substituted amidine as product. The desired halogenated amidine will be obtained by converting the hydroxyl group to a halide (e.g., bromine or iodine) using triphenylphosphine and the appropriate tetrahalomethane ($CCl_4$, $CBr_4$). This cyclic amidine can undergo further reaction with the 9-BBN functionalized CF as further described below.

The synthesis of a 9-BBN functionalized CF proceeds as follows. A hydroxylated CF is contacted with an alkenylenetrialkoxy silyl group, such as 3-(trimethoxysilyl)propyl methacrylate or (4-vinylphenyl)triethoxysilane to obtain the corresponding alkene terminated CF. contacting the alkene-functionalized CF with 9-BBN (9-Borabicyclo[3.3.1]nonane), gives the desired 9-BBN derivatized CF as illustrated in See Scheme 3.

Scheme 3

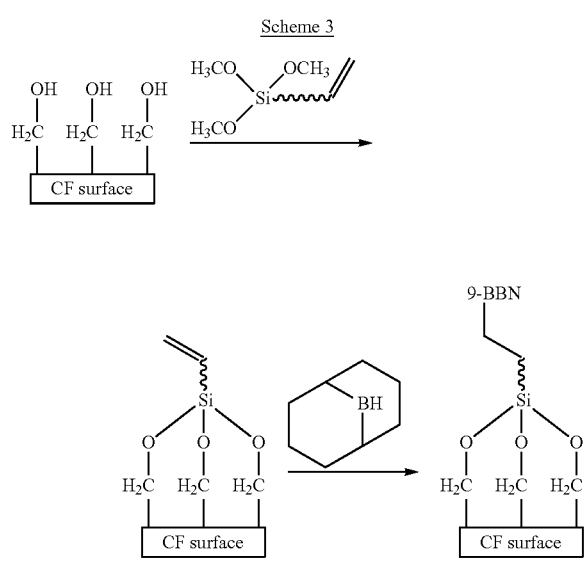

A Suziki cross-coupling reaction can be used to conjugate the above synthesized halogenated cyclic amidine to the 9-BBN derivatized CF as illustrated in Scheme 4.

Scheme 4

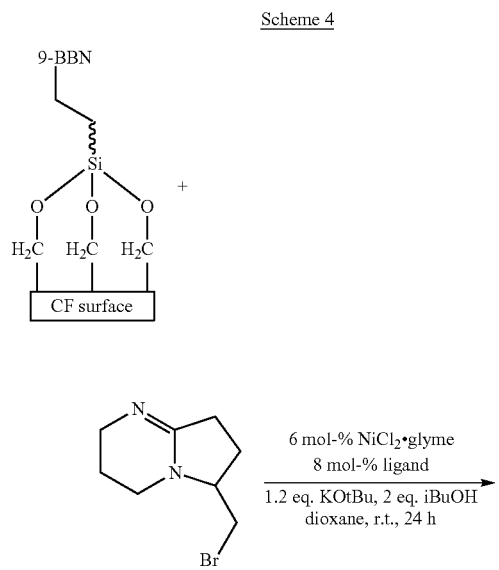

-continued

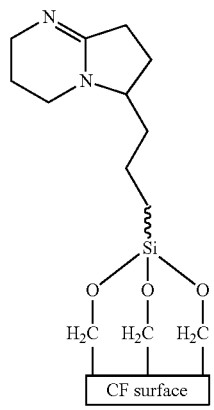

The organoamine can be directly attached to the surface of a carbon fiber or the attachment can through a linker group. In one embodiment, the organoamine moiety can be directly attached to the surface of a carbon fiber. Alternatively, a linker can be used to covalently bond the organoamine to the carbon fiber's surface. The term "linker" refers to any group that separates the organoamine moiety from the carbon fiber surface. Accordingly, a linker is a group that is covalently tethered at one end to a surface of the carbon fiber and is bound to an organoamine group at the other end. For example, the organoamine may be attached to the carbon fiber using a $(C_1-C_{10})$alkylene linker. Examples of alkylene linkers include —$(C_1-C_{10})$alkylene-NH—, —$(C_1-C_{10})$alkylenesiloxy, or a —$(C_1-C_{10})$alkylene-C(O)— linker. Polymers of ethylene glycol such as a —$(OCH_2-CH_2)_n$—O— group, where n is an integer from 0 to 10 can also be used as linkers.

Scheme 5 shows an illustrative embodiment of an organoamine functionalized carbon fiber surface.

Scheme 5

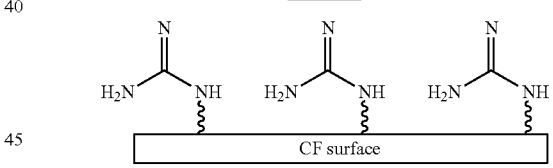

As illustrated, the organoamine group is bonded to the carbon fiber's surface using a linker. Methodologies used to covalently bond the linker to the surface functionalized carbon fiber depend on the nature of functional groups present on the surface of the fiber as well as the chemical nature of a precursor to linker group.

Thus, in one aspect of the present technology, the linker is covalently bonded to the carbon fiber through an amide bond. For instance, when the precursor of the linker desired conforms to the general formulae X—$(C_1-C_{10})$alkylene-NH$_2$ or NH$_2$—$(C_1-C_{10})$alkylene-NH$_2$, direct coupling of a carboxylic acid or an ester functionalized carbon fiber surface to the linker can be effected under conditions suitable for forming an amide bond. In the above formulae, X is a group selected from chlorine bromine, iodine, —COOH, or X is a carboxylic acid ester.

The conjugation of the linker to the fiber is promoted through the use of carboxylic acid activating agents. Examples of reagents used for forming an amide bond include without limitation dicyclohexylcarbodiimide, carbonyldiimidazole, O-(benzotriazol-1-yl)-N,N,N'N'-tetramethyluronium hexafluorophosphate (HBTU), (benzotraizol-1-yloxy)tris(dimethylamino)phosphonium hexafluorophosphate (BOP) and O-(7-azabenzotriazol-1-yl)-N,N,N'N'-tetramethyluronium hexafluorophosphate (HATU).

In an illustrative embodiment, the linker is installed using a precursor according to formula X—(C$_1$-C$_{10}$)alkylene-NH$_2$ where X is group as defined above. Scheme 6 illustratively shows a method for functionalizing the surface of a carbon fiber and then covalently bonding an organoamine group to the functionalized carbon fiber surface.

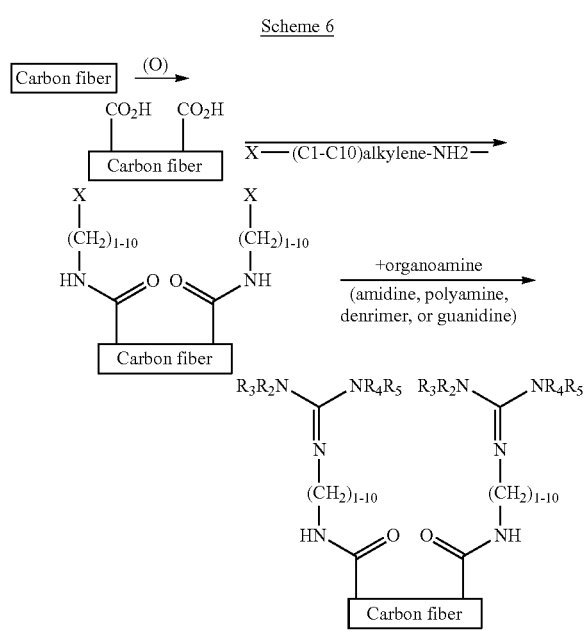

Thus, oxidative functionalization of the carbon fiber surface through chemical or electrochemical means gives a carboxylic acid functionalized carbon fiber surface. Contacting such a functionalized carbon fiber with a precursor linker group such as an amino(C$_{1-10}$)alkylene-halide provides a carbon-fiber having a covalently bonded linker. Displacement of the linker's terminal halogen group by contacting the covalently bonded linker with an appropriate organoamine provides an organoamine coated carbon fiber according to the present technology.

Alternatively, the surface carboxylic acid groups can be contacted with a diamine or a polyamine linker to manufacture an organoamine coated carbon fiber according to the present technology. For instance, the carboxylic acid functionalized fiber surface can be contacted with a Boc-protected 1,3-diaminopropane linker to provide a Boc-protected aminopropionamide functionalized carbon fiber, which can be deprotected to give an organoamine coated carbon fiber. Other polyamines such as putrescine, spermidine and spermine may also be used for the manufacture of an organoamine coated carbon fiber. Polymers, dendrimers as well as peptides having multiple amino or guanidine groups are also within the scope of organoamines suitable for use with the present technology.

According to another embodiment, the present technology provides a method for introducing an organoamine coating onto an alkylene alcohol functionalized carbon fiber, such as a methylene alcohol (—CH$_2$OH), functionalized carbon fiber using the synthetic protocol illustrated in Scheme 7.

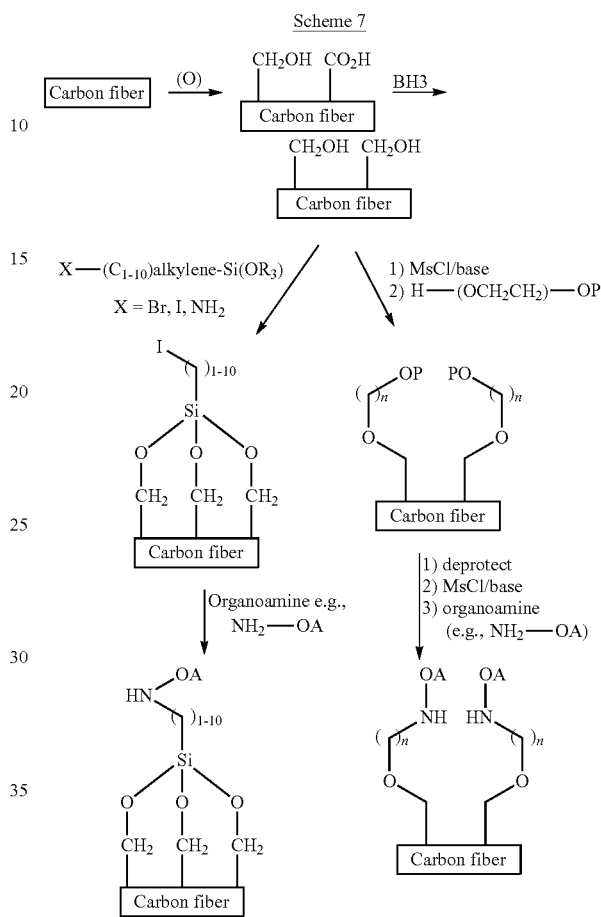

Thus, when oxidation of the carbon fiber surface results in a mixture of surface functional groups, for example, carboxylic acid groups, esters and hydroxymethyl (—CH$_2$OH) groups, the present technology provides a method for reducing the carboxylic acid and ester functional groups to hydroxymethyl groups using borane. Reaction of the resultant hydroxyl group functionalized carbon fiber with linker precursors according to formulae X—(C$_1$-C$_{10}$)alkylene-Si(OR$_3$), NH$_2$—(C$_1$-C$_{10}$)alkylene-Si(OR$_3$), and H—(OCH$_2$CH$_2$)$_n$—OP provides a linker modified carbon fiber which can subsequently be contacted with an organoamine group to provide an organoamine coated carbon fiber according to the present technology. When the precursor is X—(C$_1$-C$_{10}$)alkylene-Si(OR$_3$) or NH$_2$—(C$_1$-C$_{10}$)alkylene-Si(OR$_3$), substituent R$_3$ can be a group selected from (C$_1$-C$_{10}$)alkyl, (C$_6$-C$_{14}$)aryl, or a (C$_3$-C$_{14}$)cycloalkyl as defined above.

Examples of linker precursors within the class halo(C$_1$-C$_{10}$)alkylenetrialkoxy silane according to Formula X—(C$_1$-C$_{10}$)alkyleneSi(OR)$_3$ include without limitation include 3-bromopropyltrimethoxysilane, 3-iodopropyltrimethoxysilane, 3-bromopropyltriethoxy silane, 3-iodopropyltriethoxysilane, 4-bromobutyltrimethoxysilane, 4-iodobutyltrimethoxysilane, 4-bromobutyltriethoxysilane, 4-iodobutyltrimethoxysilane and other halogenated C$_{5-10}$ alkylenetrialkoxysilanes.

According to some embodiments a terminal amino group on the linker provides the desired amine functionalization to the surface of the carbon fiber. This is achieved by providing an appropriate precursor, for example, a precursor according to formula $NH_2—(C_1-C_{10})$alkylene $Si(OR_3)$. Examples of such precursors without limitation are 3-aminopropyltrimethoxysilane, ((6-aminohexyl)aminomethyl) triethoxysilane, or diethylaminomethyltriethoxysilane.

The present technology also provides organoamine coated carbon fibers where the organoamine is covalently attached to the fiber surface using a polymer of ethylene glycol, for example a polymer according to formula $H—(OCH_2CH_2)_n—O$, where subscript "n" is a non negative integer between 1 and 10. According to this aspect of the present technology, a methylene alcohol functionalized carbon fiber surface is first chemically transformed to a halide, tosylate, or mesylate group using routine chemical transformations. Such a chemically reactive carbon fiber is then allowed to come in contact with a polyethylene glycol precursor linker according to formula $H—(OCH_2CH_2)_n—OP$ to provide a polyethylene glycol functionalized fiber. Substituent "P" in the precursor moiety is either hydrogen or an alcohol protecting group. Examples of alcohol protecting groups include without limitation esters, ethers and silyl ether groups. The choice of the protecting group will depend on the chemistry to be employed for conjugating the linker modified carbon fiber to an organoamine. For instance, in one embodiment the terminal hydroxyl group of the polymer is protected as an acetoxy or pivaloyl group. Alternatively, the terminal hydroxyl group can be protected as a benzyl ether, a methoxymethyl ether (MOM), a β-methoxyethoxymethyl ether (MEM), or a methoxytrityl [(4-methoxyphenyl)dipenylmethyl](MMT) group. Alternatively, silyl ethers can be used as protecting groups. For instance, trimethyl silyl (TMS), t-butyldimethyl silyl (TBDMS), and triisopropyl silyl (TIPS) are suitable silyl protecting groups.

After removing the hydroxyl protecting group "P" the polyethylene glycol functionalized carbon fiber is allowed to come in contact with an organoamine under appropriate reaction conditions to provide an organoamine coated carbon fiber of the present technology.

The present technology also provides carbon fiber reinforced plastics (CFRP) by contacting the organoamine coated carbon fiber with a carboxylic acid functionalized matrix polymer. Without wishing to be bound by theory, it is believed that both electrostatic interactions and hydrogen bonding interactions may be involved in maintaining contact between the organoamine coated carbon fiber and a carbonyl functionalized matrix, for example, between the organoamine coated carbon fiber and a carboxylic acid functionalized matrix.

An illustrative embodiment of a CFRP according to this technology is schematically shown in Scheme 8. Briefly, a guanidine functionalized carbon fiber surface is brought in contact with a carboxylic acid functionalized matrix, for example, a carboxylic acid or ester functionalized matrix resin under standard conditions suitable for forming a CFRP product using the selected resin.

Scheme 8

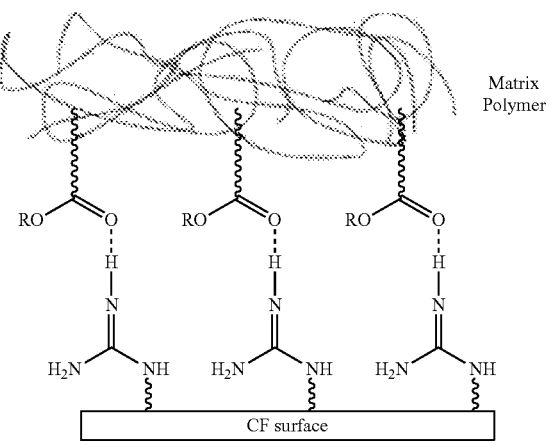

Any carbonyl or carboxylic functionalized polymer is suitable as the matrix resin. According to one embodiment, the matrix used is selected from polyesters, polyvinyl esters, polyacrylates, polyanhydrides, or copolymers of these polymers.

Examples of suitable matrix resin polymers include without limitation polyester molding resin, isophthalic polyester resin, polyglycolic acid, polylactic acid, polycaprolactum, polyethylene terephthalates, polybutylene terephthalates as well as copolymers obtained by the condensation of 4-hydroxybenzoic acid with 6-hydroxynaphthalene-2-carboxylic acid. Thermoplastic resins such as polyacetals, nylons, polyethylene terepthalate (PET), polycarbonates, polyalkylacrylates, polyurethanes and the like may also be used as the matrix resin.

The matrix resin can also be a telechelic oligomer, for example, a halato telechelic polymer. Other carbonyl or carboxylic acid containing matrix polymers include without limitation thermoplastics such as polyacetals or nylons and thermosets selected from vinyl esters and polyurethanes.

The organoamine coated carbon fibers according to the present technology has several advantages. As mentioned above, surface treatment of the carbon fiber changes the chemical nature of the fiber's surface. For instance, electrolytic or chemical oxidation of carbon fiber's surface removes weak surface layers, etches the fibers and is used to generate reactive polar functional groups on the fibers surface.

Because electrolytic and chemical treatments of the carbon fiber improve the fiber's physicochemical properties, organoamine coated fibers according to the present technology, possess greater shear resistance and tensile strength than carbon fibers obtained commercially. The organoamine coating also promotes adhesion between the fiber and the matrix resin, while permitting facile recycling of intact carbon fibers as further described below.

Carbon fibers are brittle and require protection and lubrication during handling. Lubricants and sizing materials are generally used to protect the carbon fibers. According to the present inventors, one advantage of using an organoamine coating according to the present technology is the coatings ability to function as a lubricant and sizing material to facilitate fiber handling. Moreover, depending on the pH of the manufacturing process, the organoamine coating can function as a lubricant or an antistatic and wetting agent.

For instance, when organoamine groups such as alkyl guanidines and amidines are unprotonated the organoamine coating may function as a dry lubricant that aids fiber handling and may reduce damage or breakage of the carbon fibers.

On the other hand, at a pH when the surface amine groups of the organoaminecoating are protonated, and thus ionic, the coat improves the anti-static properties of the carbon fiber. Such a carbon fiber can readily dissipate charge that may build up during handling which further prevents fiber damage.

Additionally, the ionic nature of the organoamine coating can improve solvation and enhance the suspension and wetting of the coated fibers during fiber recycling. These enhancements in solvation and wetness properties of an organoamine coated fiber are believed to increase recycling efficiency.

Another advantage of the present technology is that it permits the organoamine coating inadvertently cleaved off during fiber recycling to be easily recovered and reused. These advantages amongst others may reduce the costs associated with the manufacture of carbon fiber reinforced plastics according to the present technology.

The present technology also provides an efficient and facile recycling process that permits the recovery of carbon fibers with little or no damage or loss. Carbon fiber reinforced plastics according to the present technology are formed by strong adhesive interactions between a basic organoamine functionalized surface of a carbon fiber and polymer resins containing carbonyl or carboxylic acid surface groups.

As illustrated in Scheme 8, a combination of hydrogen bonding interactions and electrostatic interactions may be responsible of maintaining the carbon fiber-polymer resin composite. The present method permits facile recovery of carbon fibers from a carbon fiber reinforced plastic by exposing the carbon fiber reinforced plastic to an acid, such as an acidic gas in the presence of a polar solvent. Exposure to an acid promotes decomposition of the matrix polymer which is separated from the fiber. The recovered fibers can be functionalized and reused according to the present technology.

According to one embodiment, therefore, the carbon fiber reinforced plastic is exposed to an acidic gas selected from sulfur dioxide, supercritical carbon dioxide, carbonyl sulfide, carbon disulfide, boron trifluoride, nitrogen dioxide, phosphorous pentafluoride, hydrogen chloride, hydrogen fluoride, or hydrogen bromide in a polar solvent. Examples of polar solvents suitable for use during recycling include water, alcohols, organic acids, ketones, halogenated organic solvents and combinations of these solvents. For instance, the polar solvent can be selected from a $C_{1-10}$ alcohol, such as methanol, ethanol, isopropanol or butanol. Alternatively, the polar solvent is an organic acid selected from acetic acid, propionic acid, hexanoic acid as well as dicarboxylic acids such as oxalic acid, malonic acid, succinic acid and glutaric acid as examples of the dicarboxylic acid class.

Various halogenated organic solvents can also be used for recycling the carbon fibers from a carbon fiber reinforced plastic. Such halogenated organic solvents include without limitation chloroform, dichloromethane, trifluoroethanol, trichloroethylene and the like.

In an aspect of the present technology therefore, recycling is effected by contacting the carbon fiber reinforced plastic with supercritical carbon dioxide in the presence of water or a water-alcohol mixture. According to this methodology for recycling of carbon fibers, carbon dioxide forms soluble bicarbonate salts that disrupts the electrostatic and/or hydrogen bonding interactions at the interface of the organoamine coated fiber and carboxylic acid functionalized matrix polymer. This disruption of non-covalent interaction by bicarbonate releases the organoamine coated carbon fibers from the matrix polymer and permits the recovery and reuse of the carbon fibers. Because the release of the carbon fiber from the carbon fiber reinforced plastic composite is by disruption of the electrostatic and/or hydrogen bonding interactions holding the organoamine coated carbon fibers and matrix polymer together, the present technology provides a cheap and readily scalable process of recycling carbon fibers without damaging them.

EXAMPLES

The present technology is further illustrated by the following examples, which should not be construed as limiting in any way.

1. Formation of the Carbon Fiber Reinforced Plastic

The surfaces of carbon fibers is first chemically or electrochemically functionalized to introduce oxygen containing groups such as carbonyl, carboxylic acid, carboxylic acid anhydrides, alcohols and carboxylic acid ester groups.

Most commercially available carbon fibers ready for resin impregnation, however, are believed to be functionalized with such oxygen containing groups. Various methods have been described in the literature for functionalizing CF with oxygen containing groups, such as reaction with strong acids, treatment with oxygen plasma, and electrochemical oxidation. See, for example, an article by A. Brent Strong, entitled "Practical Aspects of Carbon Fiber Surface Treatment and Sizing" available on the web at http://strong.groups.et.byu.net/pages/articles/articles/surface.pdf Electrochemical treatment to functionalize the carbon fiber surface is preferred since it permits continuous processing of carbon fibers under commercial manufacturing conditions. Thus, passing the carbon fiber around a positively charged roller (anode) and into an aqueous solution of electrolytes in an electrochemical cell introduces oxygen containing functional groups onto the carbon fiber surface. If chemical functionalization protocols are used, however, carbon fibers may be oxidized by contacting the fiber with a 3:1 v/v mixture of concentrated sulfuric acid in concentrated nitric acid at about 60° C. for about 2 h. The treated fibers can be washed with deionized water until the washings are neutral, and then dried to obtain a functionalized CF. See, for example, Zhao et al. "Formation of a carbon fiber/polyhedral oligomeric silsesquioxane/carbon nanotube hybrid reinforcement and its effect on the interfacial properties of carbon fiber/epoxy composites" *Carbon* 2011 49 2624-2632.

Depending on the nature of the functional groups on the fiber's surface, appropriate chemistries are used to covalently attach an organoamine group to the carbon fiber. For instance, a carboxylic acid functionalized fiber can be contacted with an organoamine such as a diamino alkane under conditions suitable to facilitate the formation of an amide bond. Alternatively, a surface carboxylic acid group can be transformed to an ester prior to contact with a diamino alkane reagent to manufacture an organoamine coated fiber of the present technology.

The coated fiber is then contacted with a carbonyl or carboxylic acid functionalized matrix resin to manufacture a carbon fiber reinforced plastic according to the present technology. Typically, the resin polymer is used in a flowable state and is sprayed, or flowed onto the fiber surface. Alternatively, the resin polymer is injected or compressed onto the carbon fiber. The resin-fiber composite may be cured according to instructions from the manufacturer of the matrix resin used and then allowed to set prior to use.

For instance, an amidine functionalized carbon fiber can be placed in a suitable solvent such as diethyl ether, into which the carboxyl-functionalized polymer making up the matrix is mixed to form an amidinium-carboxylate carbon fiber. This material can be cured to obtain a carbon fiber reinforced plastic.

2. Recycling of Carbon Fibers from the Carbon Fiber Reinforced Plastic

Scheme 9 schematically illustrates the recycling process according to the present technology.

Scheme 9

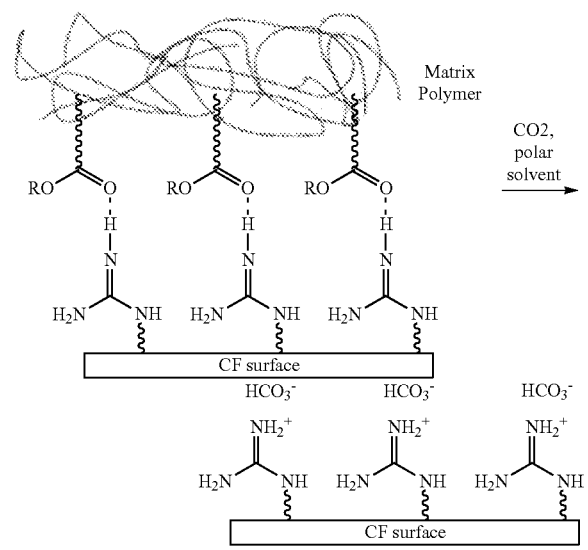

Briefly, the carbon fiber reinforced plastic is contacted with an acid, such as an acidic gas in the presence of a polar solvent to promote decomposition of the matrix and recovery of the carbon fibers. According to an embodiment of the present technology, the carbon fiber reinforced plastic is submerged in water, alcohol, or a mixture of water and an alcohol. Carbon dioxide held at supercritical temperature and pressure is passed into the solution of the carbon fiber reinforced plastic. Carbon dioxide reacts with the water used as a solvent to form bicarbonate anions which is believed disrupt the electrostatic and/or hydrogen bonding interactions between the organoamines and the carboxylic acid groups on the matrix polymer. This results in the decomposition and separation of the matrix polymer which facilitates the release and recovery of the carbon fibers.

In another embodiment, a suspension of the carbon fiber reinforced plastic in water, alcohol, or a mixture of water and alcohol is contacted with subcritical but high concentrations of carbon dioxide. Carbon dioxide can be provided as a liquid or as a solution of the gas in an appropriate solvent. For certain embodiments, the carbon fiber reinforced plastic is contacted with carbon dioxide at a pressure in the range from about 5 atmospheres to about 100 atmospheres, for example, about 10 atmospheres, about 20 atmospheres, about 30 atmospheres, about 40 atmospheres, about 50 atmospheres, about 60 atmospheres, about 70 atmospheres, about 80 atmospheres, or about 90 atmospheres. For instance, the carbon fiber reinforced plastic can be contacted with carbon dioxide at about 65 atmospheres, about 70 atmospheres, about 73 atmospheres, about 79 atmospheres, about 83 atmospheres, or about 86 atmospheres.

Recycling using carbon dioxide is carried out at temperatures in the range from about 0° C. to about 32° C. According to one embodiment, recycling is carried out at a temperature of about 5° C., about 10° C., about 15° C., about 20° C., about 25° C., about 30° C., or about 31° C. For certain embodiments, recycling is carried out at about 25° C., about 26° C., about 27° C., about 28° C., about 28.5° C., about 29° C., about 29.5° C., about 30° C., about 30.1° C., about 30.2° C., about 30.3° C., about 30.4° C., about 30.5° C., about 30.6° C., about 30.7° C., about 30.8° C., about 30.9° C., about 31° C., about 31.1° C., about 31.2° C., about 31.3° C., about 31.4° C., or about 31.5° C. In one embodiment, the recycling is carried out by contacting the carbon fiber reinforced plastic with carbon dioxide at a pressure equal to or greater than about 73 atmospheres and a temperature equal to or greater than about 31.1 C.

Because of its low toxicity and environmental friendliness supercritical $CO_2$ is becoming an important commercial and industrial solvent. Additionally, recycling of carbon fibers according to the present technology is carried out under relatively mild conditions at relatively low temperatures that permits the carbon fibers to be extracted from the matrix polymer with little or no damage to the structural integrity of the recovered fiber.

Analysis of damage to the fiber obtained using the recycling method of the present technology can readily be performed using conventional spectroscopic techniques known in the art, including X-ray photon spectroscopy (XPS). XPS permits a quantitative determination of organoamine coating lost from the fibers surface during recycling and also permits characterization and quantitation of the nature and concentration respectively of carbonyl groups on the surface of the carbon fiber. While re-functionalization of the fiber surface or a new coating of an organoamine may be desirable on occassion, the gentleness of the present recycling methodology may permit recovery of carbon fibers in an undamaged form in high yield.

EQUIVALENTS

The present disclosure is not to be limited in terms of the particular embodiments described in this application. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group. As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A carbon fiber reinforced plastic matrix, comprising:
   at least one surface functionalized carbon fiber; and
   at least one carboxylic acid functionalized matrix polymer;
   wherein
      the carbon fiber is surface functionalized with one or more organoamines selected from a diethylamine, amidine, diguanidine, guanidine, amine dendrimer, or polyguanidine group.

2. The carbon fiber reinforced plastic matrix of claim 1, wherein the organoamine is attached to the carbon fiber with a linker comprising a ($C_1$-$C_{10}$)alkylene group.

3. The carbon fiber reinforced plastic matrix of claim 2, wherein the linker is a —($C_1$-$C_{10}$)alkylenesiloxy, —($C_1$-$C_{10}$)alkylene-C(O)—, or a —(OCH$_2$—CH$_2$)$_n$—O— group, where n is an integer from 1 to 10.

4. The carbon fiber reinforced plastic matrix of claim 1, wherein the organoamine is selected from the group consisting of 1,1'-((ethylimino)bis(trimethylene))diguanidine and a guanidine dendrimer.

5. The carbon fiber reinforced plastic matrix of claim 1, wherein the matrix polymer is a thermoset polymer selected from the group consisting of polyester, polyvinyl ester, polyurethane and copolymers thereof.

6. The carbon fiber reinforced plastic matrix of claim 1, wherein the matrix polymer is a thermoplastic polymer selected from the group consisting of polyacetals, nylons, polyethylene terephthalate (PET) and copolymers thereof.

7. A method for making a carbon fiber reinforced plastic matrix, the method comprising:
   contacting at least one surface functionalized carbon fiber with at least one carboxylic acid functionalized matrix polymer to obtain the carbon fiber reinforced plastic matrix,
   wherein the carbon fiber is surface functionalized with one or more organoamines selected from a diethylamine, amidine, diguanidine, guanidine, amine dendrimer, or polyguanidine group.

8. The method of claim 7, wherein the one or more organoamines of the surface functionalized carbon fiber are attached to the carbon fiber with a linker comprising a ($C_1$-$C_{10}$)alkylene group.

9. The method of claim 7, further comprising:
   oxidizing at least one surface of a carbon fiber to provide a carboxylic acid functionalized carbon fiber; and
   contacting the carboxylic acid functionalized carbon fiber with one or more organoamines or organoamine precursors to provide the carbon fiber surface functionalized with one or more organoamines.

10. The method of claim 7 further comprising:
    oxidizing at least one surface of a carbon fiber to provide a mixture of carboxylic acid and ester groups on the carbon fiber surface;
    hydrolyzing the ester groups to carboxylic acid groups to provide a carboxylic acid functionalized carbon fiber; and
    contacting the carboxylic acid functionalized carbon fiber with the one or more organoamines or organoamine precursors to provide the carbon fiber surface functionalized with one or more organoamines.

11. The method of claim 7, further comprising:
    oxidizing at least one surface of a carbon fiber to provide a mixture of carboxylic acid and ester groups on the carbon fiber surface;
    reducing the mixture of carboxylic acid and ester groups on the carbon fiber surface to hydroxyl groups; and
    contacting hydroxyl groups with one or more organoamine precursors to provide the carbon fiber surface functionalized with one or more organoamines.

12. A method for recycling a carbon fiber reinforced plastic matrix, the method comprising:
    contacting the carbon fiber reinforced plastic matrix with an acid;
    decomposing the matrix to provide a decomposed matrix and carbon fiber; and
    separating the decomposed matrix from the carbon fiber to obtain recycled carbon fiber;
    wherein
       the carbon fiber reinforced plastic matrix comprises at least one surface functionalized carbon fiber and at least one carboxylic acid functionalized matrix polymer; and
       the carbon fiber is surface functionalized with one or more organoamines selected from a diethylamine, amidine, diguanidine, guanidine, amine dendrimer, or polyguanidine group.

13. The method of claim 12, wherein the organoamine of the surface functionalized carbon fiber is attached to the carbon fiber with a linker comprising a ($C_1$-$C_{10}$)alkylene group.

14. The method of claim 12, wherein contacting the carbon fiber reinforced plastic matrix with an acid occurs in the presence of a polar protic solvent.

15. The method of claim 14, wherein the polar protic solvent of the contacting step is water, a linear or branched ($C_1$-$C_{10}$) alcohol, a carboxylic acid, or mixtures thereof.

16. The method of claim 12, wherein the acid of the contacting step is an acidic gas.

17. The method of claim 16, wherein the acidic gas of the contacting step is sulfur dioxide, supercritical carbon dioxide, carbonyl sulfide, carbon disulfide, boron trifluoride, nitrogen dioxide, phosphorous pentafluoride, hydrogen chloride, hydrogen fluoride, or hydrogen bromide.

18. The method of claim 12, further comprising re-functionalization of the surface of the recycled carbon fiber after the separating step.

19. The carbon fiber reinforced plastic matrix of claim 1, wherein the organoamine is selected from the group consisting of an amidine, diguanidine, guanidine, amine dendrimer, and a polyguanidine group.

* * * * *

UNITED STATES PATENT AND TRADEMARK OFFICE
CERTIFICATE OF CORRECTION

| | |
|---|---|
| PATENT NO. | : 8,877,872 B2 |
| APPLICATION NO. | : 13/882424 |
| DATED | : November 4, 2014 |
| INVENTOR(S) | : Anderson et al. |

It is certified that error appears in the above-identified patent and that said Letters Patent is hereby corrected as shown below:

On the Title Page, in item (56), under "OTHER PUBLICATIONS", in Column 2, Line 22, delete "CO2" and insert -- $CO_2$ --, therefor.

On the Title Page, in item (56), under "OTHER PUBLICATIONS", in Column 2, Line 33, delete "silsesquioxanejcarbon" and insert -- silsesquioxanecarbon --, therefor.

On the Title Page, in item (57), under "ABSTRACT", in Column 2, Line 1, delete "an carbon" and insert -- a carbon --, therefor.

In the Specification

In Column 1, Line 7, delete "claims the benefit" and insert -- is a national stage filing under 35 U.S.C. §371 --, therefor.

In Column 1, Lines 61-62, delete "-($OCH_2$-$CH_2$)-O-" and insert -- -($OCH_2$-$CH_2$)$_n$-O- --, therefor.

In Column 4, Line 24, delete "iso-propoylamine," and insert -- iso-propylamine, --, therefor.

In Column 4, Line 52, delete "o-tohuidine," and insert -- o-toluidine, --, therefor.

In Column 5, Line 25, delete "pyrazinyl thiophenyl" and insert -- pyrazinyl, thiophenyl, --, therefor.

In Column 5, Line 29, delete "beuzoxazolyl," and insert -- benzoxazolyl, --, therefor.

In Column 6, Lines 9-10, delete "($C_1$-$C_{10}$)alkyl($C_3$-$C_{14}$)cycloalkyl," and insert -- ($C_1$-$C_{10}$)alkyl, ($C_3$-$C_{14}$)cycloalkyl, --, therefor.

Signed and Sealed this
Fourth Day of August, 2015

Michelle K. Lee
*Director of the United States Patent and Trademark Office*

CERTIFICATE OF CORRECTION (continued)
U.S. Pat. No. 8,877,872 B2

In Column 6, Line 14, delete "-Si(R$_6$), -O-" and insert -- -Si(R$_6$)$_2$-O- --, therefor.

In Column 6, Line 18, delete "N,N,N'N'tetramethyl-N"," and insert -- N,N,N'N'-tetramethyl-N", --, therefor.

In Column 6, Lines 22-23, delete "Alternatively." and insert -- Alternatively, --, therefor.

In Column 6, Line 42, delete "(Si(C$_6$H$_5$)$_2$-O)" and insert -- {Si(C$_6$H$_5$)$_2$-O} --, therefor.

In Column 9, Line 38, delete "Suziki" and insert -- Suzuki --, therefor.

In Column 11, Line 20, delete " $\overline{X\!-\!\!-\!(C1\text{-}C10)\text{alkylene-NH2}\!-\!\!-\!\!\longrightarrow}$ " and insert -- $\overline{X\!-\!\!-\!(C_1\text{-}C_{10})\text{alkylene-NH}_2\!-\!\!-\!\!\longrightarrow}$ --, therefor.

In Column 12, Line 9, delete " $\xrightarrow{BH3}$ " and insert -- $\xrightarrow{BH_3}$ --, therefor.

In Column 14, Line 29, delete "polycaprolactum," and insert -- polycaprolactam, --, therefor.

In Column 14, Line 34, delete "terepthalate" and insert -- terephthalate --, therefor.

In Column 16, Lines 30-31, delete "http://strong.groups.et.byu.net/pages/articles/articles/surface.pdf" and insert -- http://strong.groups.et.byu.net/pages/articles/articles/surface.pdf. --, therefor.

In Column 17, Lines 19-21, delete " $\xrightarrow{\text{CO2, polar solvent}}$ " and insert -- $\xrightarrow{\text{CO}_2,\text{ polar solvent}}$ --, therefor.